US010422757B2

(12) United States Patent
Sugimoto et al.

(10) Patent No.: US 10,422,757 B2
(45) Date of Patent: Sep. 24, 2019

(54) X-RAY INSPECTION DEVICE

(71) Applicant: ISHIDA CO., LTD., Kyoto-shi, Kyoto (JP)

(72) Inventors: Kazuyuki Sugimoto, Ritto (JP); Kazuhiro Suhara, Ritto (JP)

(73) Assignee: ISHIDA CO., LTD., Kyoto (JP)

(*) Notice: Subject to any disclaimer, the term of this patent is extended or adjusted under 35 U.S.C. 154(b) by 0 days.

(21) Appl. No.: 16/326,547

(22) PCT Filed: Aug. 3, 2017

(86) PCT No.: PCT/JP2017/028304
§ 371 (c)(1),
(2) Date: Feb. 19, 2019

(87) PCT Pub. No.: WO2018/034170
PCT Pub. Date: Feb. 22, 2018

(65) Prior Publication Data
US 2019/0212280 A1 Jul. 11, 2019

(30) Foreign Application Priority Data
Aug. 19, 2016 (JP) ................................. 2016-161458

(51) Int. Cl.
G01N 23/18 (2018.01)
G01N 23/04 (2018.01)
(Continued)

(52) U.S. Cl.
CPC ............. *G01N 23/18* (2013.01); *G01N 23/04* (2013.01); *G06T 7/0004* (2013.01); *H05G 1/10* (2013.01);
(Continued)

(58) Field of Classification Search
CPC .......... G01N 23/18; G01N 23/04; H05G 1/30; H05G 1/10; G06T 7/0004; G06T 2207/10116
See application file for complete search history.

(56) References Cited

U.S. PATENT DOCUMENTS

| 6,430,258 B1* | 8/2002 | Spaak | ...................... H05G 1/30 378/95 |
| 2012/0132825 A1* | 5/2012 | Amitani | ................... A61B 6/00 250/394 |
| 2015/0257245 A1* | 9/2015 | Tajima | .................. A61B 6/542 378/62 |

FOREIGN PATENT DOCUMENTS

| JP | 10185841 A | * 7/1998 | ........... G01V 5/0016 |
| JP | H10-185841 A | 7/1998 | |

(Continued)

OTHER PUBLICATIONS

Translation of the Written Opinion of the International Searching Authority, dated Nov. 7, 2017.

*Primary Examiner* — Michael C Bryant
(74) *Attorney, Agent, or Firm* — Global IP Counselors, LLP

(57) ABSTRACT

An X-ray inspection apparatus includes an X-ray irradiation unit that irradiates an article with X-rays, an X-ray detection unit that detects the X-rays transmitted through the article, an inspection unit that generates an X-ray transmission image of the article based on a signal output from the X-ray detection unit and performs inspection of the article based on the X-ray transmission image, and a control unit that controls the X-ray irradiation unit and the X-ray detection unit. The control unit executes a first control of controlling the X-ray irradiation unit such that an irradiation output is increased if a detection output of the X-ray detection unit is decreased when the control unit controls the X-ray irradia- (Continued)

tion unit such that the irradiation output of the X-ray irradiation unit becomes a first irradiation output. The control unit executes the first control in a state where the article is not irradiated with the X-rays.

5 Claims, 3 Drawing Sheets

(51) Int. Cl.
*H05G 1/30* (2006.01)
*G06T 7/00* (2017.01)
*H05G 1/10* (2006.01)

(52) U.S. Cl.
CPC ...... *H05G 1/30* (2013.01); *G06T 2207/10116* (2013.01)

(56) References Cited

FOREIGN PATENT DOCUMENTS

| | | |
|---|---|---|
| JP | 2001004560 A | 1/2001 |
| JP | 2004-020442 A | 1/2004 |
| JP | 2011-209177 A | 10/2011 |
| JP | 2012-198074 A | 10/2012 |
| JP | 2013-160569 A | 8/2013 |

* cited by examiner

|  | INPUT CURRENT(mA) | SENSITIVITY | DETECTION OUTPUT (COUNTS) |
|---|---|---|---|
| TEST VALUE | 1.0 | 1 | 150 |
| FIRST MODE | 5.0 | 4 | 3000 |
| SECOND MODE | 10.0 (MAXIMUM VALUE) | 2 | 3000 |

X-RAY INSPECTION DEVICE

CROSS-REFERENCE TO RELATED APPLICATIONS

This U.S. National stage application claims priority under 35 U.S.C. § 119(a) to Japanese Patent Application No. 2016-161458, filed in Japan on Aug. 19, 2016, the entire contents of which are hereby incorporated herein by reference.

TECHNICAL FIELD

The present disclosure relates to an X-ray inspection apparatus.

BACKGROUND ART

An X-ray inspection apparatus, including an X-ray irradiation unit that irradiates an article with X-rays, an X-ray detection unit that detects the X-rays transmitted through the article, an inspection unit that generates an X-ray transmission image of the article based on a signal output from the X-ray detection unit and performs inspection of the article based on the X-ray transmission image, and a control unit that controls the X-ray irradiation unit and the X-ray detection unit is known as an X-ray inspection apparatus (for example, see Japanese Unexamined Patent Publication No. 2001-4560). The control unit in the X-ray inspection apparatus described in Patent Literature 1 corrects a sensitivity of the X-ray detection unit in response to changing with time lapse of the X-ray irradiation unit and the X-ray detection unit.

SUMMARY OF INVENTION

Technical Problem

In the X-ray inspection apparatus, from the viewpoint of attaching importance to the inspection performance of the article, it is common to adjust the sensitivity of the X-ray detection unit after controlling the X-ray irradiation unit such that the irradiation output of the X-ray irradiation unit becomes a maximum value. However, the higher the output of the X-ray irradiation unit is, the faster the deterioration of the X-ray irradiation unit and the X-ray detection unit progresses. Therefore, it is required to suppress the deterioration of the X-ray irradiation unit and the X-ray detection unit while securing the inspection performance of the article.

An object of the present disclosure is to provide an X-ray inspection apparatus capable of suppressing deterioration of an X-ray irradiation unit and an X-ray detection unit while securing an inspection performance of an article.

Solution to Problem

According to one embodiment of the present disclosure, there is provided an X-ray inspection apparatus including: an X-ray irradiation unit that irradiates an article with X-rays; an X-ray detection unit that detects the X-rays transmitted through the article; an inspection unit that generates an X-ray transmission image of the article based on a signal output from the X-ray detection unit and performs inspection of the article based on the X-ray transmission image; and a control unit that controls the X-ray irradiation unit and the X-ray detection unit, in which, the control unit executes a first control of controlling the X-ray irradiation unit such that an irradiation output is increased, if a detection output of the X-ray detection unit is decreased when the control unit controls the X-ray irradiation unit such that the irradiation output of the X-ray irradiation unit becomes a first irradiation output.

In the X-ray inspection apparatus, there is a possibility that deterioration of the X-ray irradiation unit or the X-ray detection unit is progressing, if the detection output of the X-ray detection unit is decreased when the control unit controls the X-ray irradiation unit such that the irradiation output of the X-ray irradiation unit becomes the first irradiation output. At this time, the deterioration of the X-ray irradiation unit and the X-ray detection unit is suppressed, as compared with a case where the irradiation output of the X-ray irradiation unit is a maximum value, if a sensitivity of the X-ray detection unit is previously set to be relatively high and the first irradiation output of the X-ray irradiation unit is set to be smaller than a maximum value, for example. Also, the control unit executes the first control to secure room for increasing the irradiation output of the X-ray irradiation unit so that it is possible to prevent the inspection performance of the article from being reduced. Therefore, it is possible to suppress the deterioration of the X-ray irradiation unit and the X-ray detection unit while securing the inspection performance of the article.

In the X-ray inspection apparatus according to one embodiment of the present disclosure, the control unit may execute the first control in a state where the article is not irradiated with X-rays emitted by the X-ray irradiation unit and the X-ray detection unit is detecting the X-rays with which the article is not irradiated. In this case, it is highly likely that the detection output of the X-ray detection unit is decreased due to the deterioration of the X-ray irradiation unit or the X-ray detection unit, as compared with a state where the X-ray detection unit detects the X-rays transmitted through the article. Therefore, the control unit can appropriately execute the first control.

In the X-ray inspection apparatus according to one embodiment of the present disclosure, the control unit may execute a second control of controlling the X-ray detection unit such that the detection output is increased, if the detection output is decreased when the control unit controls the X-ray irradiation unit such that the irradiation output becomes a second irradiation output larger than the first irradiation output, and the first control and the second control may be switchable. In this case, an operator of the X-ray inspection apparatus can select either the first control in which the irradiation output of the X-ray irradiation unit is suppressed or the second control in which the irradiation output of the X-ray irradiation unit is enhanced.

In the X-ray inspection apparatus according to one embodiment of the present disclosure, in the second control, the control unit may increase the detection output by increasing a sensitivity, if the detection output is decreased when the control unit sets the sensitivity of the X-ray detection unit to a second sensitivity and simultaneously controls the X-ray irradiation unit such that an input current to the X-ray irradiation unit becomes a maximum value, and in the first control, the control unit may increase the irradiation output by increasing the input current, if the detection output is decreased when the control unit sets the sensitivity to a first sensitivity higher than the second sensitivity and simultaneously controls the X-ray irradiation unit such that the input current becomes a first input current smaller than the maximum value. In this case, since the control unit executes the first control of controlling the X-ray irradiation unit with the input current to the X-ray irradiation unit, which is smaller than the maximum value, it is possible to reduce the power consumption of the X-ray irradiation unit.

The X-ray inspection apparatus according to one embodiment of the present disclosure may further include: a display unit that displays a time during which the control unit is executing the first control and information on the irradiation output of the X-ray irradiation unit controlled by the first control. In this case, the operator of the X-ray inspection apparatus can confirm that the deterioration of the X-ray irradiation unit and the X-ray detection unit is suppressed, on the display unit.

Effects of Invention

According to the present disclosure, it is possible to suppress the deterioration of the X-ray irradiation unit and the X-ray detection unit while securing the inspection performance of the article.

DESCRIPTION OF EMBODIMENTS

Figure 1:
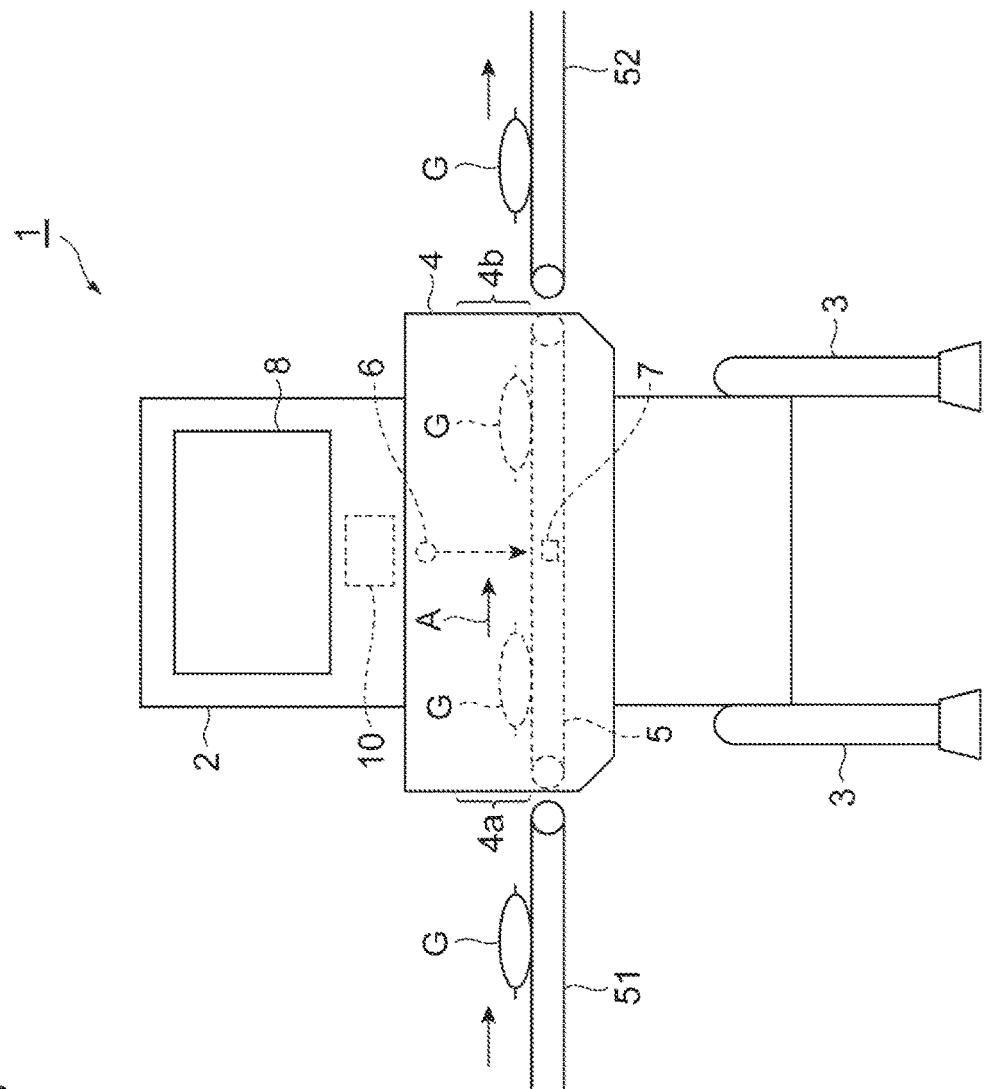
FIG. 1 is a configuration diagram of an X-ray inspection apparatus according to an embodiment of the present disclosure.

Hereinafter, an embodiment of the present disclosure will be described in detail with reference to the drawings. Incidentally, in each drawing, the same or corresponding parts are denoted by the same reference numerals, and descriptions thereof will not be repeated.

As illustrated in FIG. 1, an X-ray inspection apparatus 1 includes an apparatus main body 2, a support leg 3, a shield box 4, a transport conveyor 5, an X-ray irradiation unit 6, an X-ray detection unit 7, a display operation unit (display unit) 8, and a control unit 10. The X-ray inspection apparatus 1 acquires an X-ray transmission image of an article G while transporting the article G, and performs inspection (for example, inspection of storage number, inspection of foreign body inclusion, inspection of a defective article, inspection of chipping, and the like) of the article G based on the X-ray transmission image. The X-ray inspection apparatus 1 is connected to an external power supply (not illustrated). The external power supply supplies electric power for performing the inspection of the article G to the X-ray inspection apparatus 1.

Note that the article G before the inspection is carried into the X-ray inspection apparatus 1 by a carry-in conveyor 51, and the article G after the inspection is carried out from the X-ray inspection apparatus 1 by a carry-out conveyor 52. The article G which is determined as a defective article by the X-ray inspection apparatus 1 is sorted outside a production line by a sorting apparatus (not illustrated) disposed on the downstream side of the carry-out conveyor 52, and the article G which is determined as a good article by the X-ray inspection apparatus 1 passes through the sorting apparatus as it is.

The apparatus main body 2 houses the control unit 10 and the like. The support leg 3 supports the apparatus main body 2. The shield box 4 is provided in the apparatus main body 2 and prevents a leakage of X-rays. In the shield box 4, a carry-in port 4a and a carry-out port 4b are formed. The article G before the inspection is carried from the carry-in conveyor 51 to the inside of the shield box 4 through the carry-in port 4a, and, the article G after the inspection is carried out from the inside of the shield box 4 to the carry-out conveyor 52 through the carry-out port 4b. An X-ray shielding curtain (not illustrated) for preventing the leakage of X-rays is provided at each of the carry-in port 4a and the carry-out port 4b.

The transport conveyor 5 is disposed inside the shield box 4 and transports the article G along a transport direction A from the carry-in port 4a to the carry-out port 4b. The transport conveyor 5 is, for example, a belt conveyor stretched between the carry-in port 4a and the carry-out port 4b.

The X-ray irradiation unit 6 is disposed inside the shield box 4 and irradiates the article G transported by the transport conveyor 5 with X-rays. The X-ray irradiation unit 6 includes, for example, an X-ray tube (not illustrated) that emits X-rays and a collimator that spreads X-rays emitted from the X-ray tube in a fan shape on a plane perpendicular to the transport direction A.

An input current (so-called tube current) is input to the X-ray tube of the X-ray irradiation unit 6 at a predetermined rated voltage (for example, 50 kV) by electric power supplied from the external power supply. The X-ray tube of the X-ray irradiation unit 6 outputs X-rays having an irradiation output according to the input current. The irradiation output of the X-ray irradiation unit 6 is an intensity of X-rays output from the X-ray tube according to an input current input to the X-ray tube of the X-ray irradiation unit 6. A maximum value of the input current is a predetermined rated current (for example, 10.0 mA). The input current can be optionally set with the maximum value as an upper limit. The irradiation output of the X-ray irradiation unit 6 becomes larger as the input current increases and becomes smaller as the input current decreases.

The X-ray tube of the X-ray irradiation unit 6 deteriorates according to an irradiation time of the X-rays and an irradiation intensity of the X-rays. Generally, the intensity of the X-rays emitted by the X-ray tube (that is, the irradiation output of the X-ray irradiation unit 6) becomes larger as the input current increases and becomes smaller as the input current decreases. For this reason, the deterioration of the X-ray tube of the X-ray irradiation unit 6 progresses faster as the input current increases and progresses slower as the input current decreases.

The X-ray detection unit 7 is disposed inside the shield box 4 and detects X-rays transmitted through the article G and the transport conveyor 5. The X-ray detection unit 7 is configured as, for example, a line sensor. Specifically, the X-ray detection unit 7 includes a plurality of photodiodes disposed one-dimensionally along a horizontal direction perpendicular to the transport direction A, and a scintillator disposed on an incident side of the X-ray with respect to each photodiode. In this case, in the X-ray detection unit 7, the X-rays incident on the scintillator are converted into light, and the light incident on each photodiode is converted into an electric signal.

The X-rays emitted from the X-ray tube of the X-ray irradiation unit 6 are incident on the X-ray detection unit 7. The X-ray detection unit 7 detects X-rays having an intensity according to the irradiation output of the X-ray irradiation unit 6 with a set sensitivity. The sensitivity of the X-ray detection unit 7 is set by the control unit 10 described later. The detection output of the X-ray detection unit 7 is the intensity of X-rays detected by the X-ray detection unit 7 with the sensitivity. In a case where the intensity of the incident X-rays is constant, the detection output of the X-ray detection unit 7 becomes larger as the sensitivity of the X-ray detection unit 7 increases and becomes smaller as the sensitivity of the X-ray detection unit 7 decreases. The detection output of the X-ray detection unit 7 is represented by, for example, the count number of X-ray photons (count per second (cps) and the like).

The X-ray detection unit 7 deteriorates according to an incidence time of the X-rays and an incidence intensity of the X-rays. Generally, the deterioration of the X-ray detection unit 7 progresses faster as the incidence intensity of the X-rays increases, and progresses slower as the incidence intensity of the X-rays decreases. That is, generally, the deterioration of the X-ray detection unit 7 progresses faster as an input current to the X-ray irradiation unit 6 increases, and progresses slower as the input current to the X-ray irradiation unit 6 decreases.

The display operation unit 8 is provided in the apparatus main body 2, and displays various information and accepts input of various conditions and the like. The display operation unit 8 is, for example, a liquid crystal display and displays an operation screen as a touch panel. In this case, it is possible for the operator to input various conditions including a switching selection between a first mode and a second mode, as described later, though the display operation unit 8. Also, as described later, the display operation unit 8 displays a time during which the control unit 10 is executing a first control and information on the irradiation output of the X-ray irradiation unit 6 controlled by the first control.

The control unit 10 is disposed inside the apparatus main body 2 and controls an operation of each part of the X-ray inspection apparatus 1. The control unit 10 is configured with a central processing unit (CPU), a read only memory (ROM), a random access memory (RAM), and the like. A signal, which has been output from the X-ray detection unit 7 and subjected to A/D conversion, is input to the control unit 10. The control unit 10 functions as an inspection unit, which generates an X-ray transmission image of the article G based on the signal and performs the inspection of the article G based on the X-ray transmission image.

The control unit 10 controls the X-ray irradiation unit 6 and the X-ray detection unit 7. The control unit 10 is a circuit configured to execute calibration processing in order to appropriately perform the inspection of the article G. The calibration processing is a processing of setting the input current to the X-ray irradiation unit 6 and the sensitivity of the X-ray detection unit 7 such that the detection range of the detection output of the X-ray detection unit 7 is within a predetermined range (hereinafter, also referred to as an inspection range). In this calibration processing, the control unit 10 sets the input current to the X-ray irradiation unit 6 and the sensitivity of the X-ray detection unit 7 such that the detection range of the count number of X-ray photons falls within the inspection range (for example, zero counts to 3000 counts).

The calibration processing includes a first mode and a second mode. The first mode is a mode (so-called economy mode) in which there is performed calibration processing for suppressing the irradiation output of the X-ray irradiation unit 6 to suppress deterioration of the X-ray irradiation unit 6 and the X-ray detection unit 7 and to reduce a power consumption amount of the X-ray irradiation unit 6. The second mode is a mode (so-called normal mode) in which there is performed calibration processing for enhancing the irradiation output of the X-ray irradiation unit 6 to sharpen the X-ray transmission image of the article G. The first mode and the second mode are switchable, for example, based on a selection operation through the display operation unit 8 by the operator.

In the first mode, the control unit 10 sets an input current to the X-ray irradiation unit 6 to a first input current, in a state where the sensitivity of the X-ray detection unit 7 is fixed to a first sensitivity. In the first mode, the control unit 10 executes a first control of controlling the X-ray irradiation unit 6 such that the irradiation output of the X-ray irradiation unit 6 is increased, if the detection output of the X-ray detection unit 7 is decreased when the control unit 10 controls the X-ray irradiation unit 6 such that the irradiation output of the X-ray irradiation unit 6 becomes a first irradiation output. The first irradiation output is the intensity of X-rays output from the X-ray tube in a state where the input current input to the X-ray tube of the X-ray irradiation unit 6 is set to the first input current.

In the second mode, the control unit 10 sets the sensitivity of the X-ray detection unit 7 to a second sensitivity, in a state where the irradiation output of the X-ray irradiation unit 6 is fixed to a second irradiation output larger than the first irradiation output. In the second mode, the control unit 10 executes a second control of controlling the X-ray detection unit 7 such that the detection output of the X-ray detection unit 7 is increased, if the detection output of the X-ray detection unit 7 is decreased when the control unit 10 controls the X-ray irradiation unit 6 such that the irradiation output of the X-ray irradiation unit 6 becomes the second irradiation output. The second irradiation output is the intensity of X-rays output from the X-ray tube in a state where the input current input to the X-ray tube, of the X-ray irradiation unit 6 is a second input current larger than the first input current. As an example, the second input current is the predetermined rated current (that is, the maximum value of the input current) of the X-ray tube.

For example, the control unit 10 executes the first control and the second control under a certain condition that factors causing the irradiation output of the X-ray irradiation unit 6 and the detection output of the X-ray detection unit 7 to fluctuate are reduced. The certain condition is a condition for operating an X-ray inspection apparatus 1 such that, if the irradiation output of the X-ray irradiation unit 6 is substantially constant, the detection output of the X-ray detection unit 7 is substantially constant according to the irradiation output of the X-ray irradiation unit 6. The certain condition includes a state where the article G is not irradiated with X-rays omitted by the X-ray irradiation unit 6 and the X-ray detection unit 7 is detecting, the X-rays with which the article G is not irradiated. As an example, the certain condition is a state where the X-ray detection unit 7 is detecting the X-rays emitted by the X-ray irradiation unit 6 after starting up the X-ray inspection apparatus 1 and before starting the inspection of the article G by the X-ray inspection apparatus 1. Under the certain condition, since the article G is not interposed between the X-ray irradiation unit 6 and the X-ray detection unit 7, it is highly likely that the detection output of the X-ray detection unit 7 is decreased due to the deterioration of the X-ray irradiation unit 6 or the X-ray detection unit 7, as compared with a case where the X-ray detection unit 7 detects X-rays transmitted through the article G in the present embodiment, the control unit 10 executes the calibration processing under the certain condition.

Next, the calibration processing executed by the control unit 10 will be described with reference to FIG. 2 and FIG. 3.

As a first stage of the calibration processing, the control unit 10 acquires a relationship between the irradiation output of the X-ray irradiation unit 6 and the detection output of the X-ray detection unit 7, with the input current to the X-ray irradiation unit 6 and the sensitivity of the X-ray detection unit 7 such that the detection output of the X-ray detection unit 7 becomes a test detection output smaller than an upper limit value (for example, 3000 counts) of the inspection range.

Figure 2:
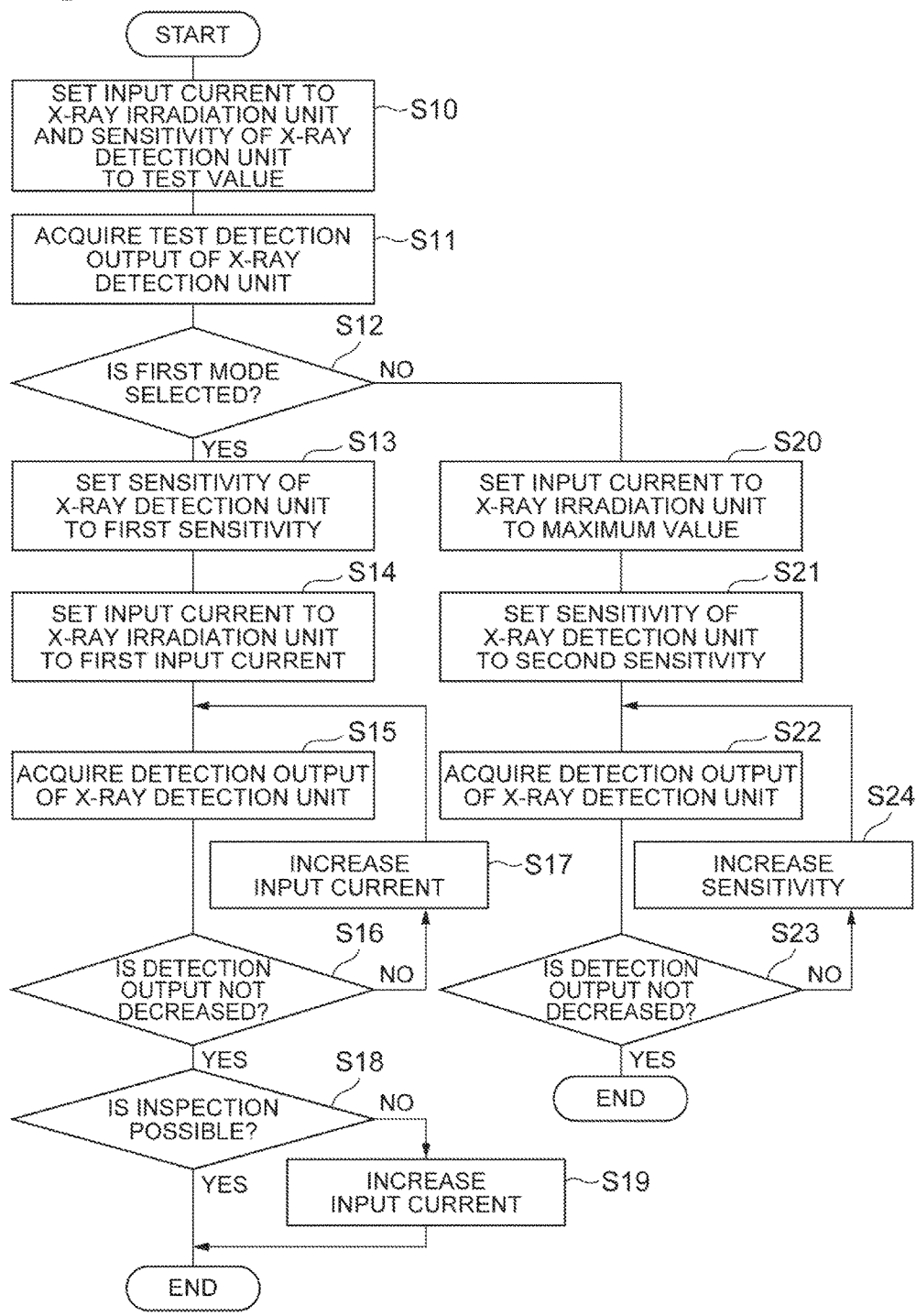
FIG. 2 is a flowchart showing calibration processing of the X-ray inspection apparatus of FIG. 1.
Figures 3A, 3B:
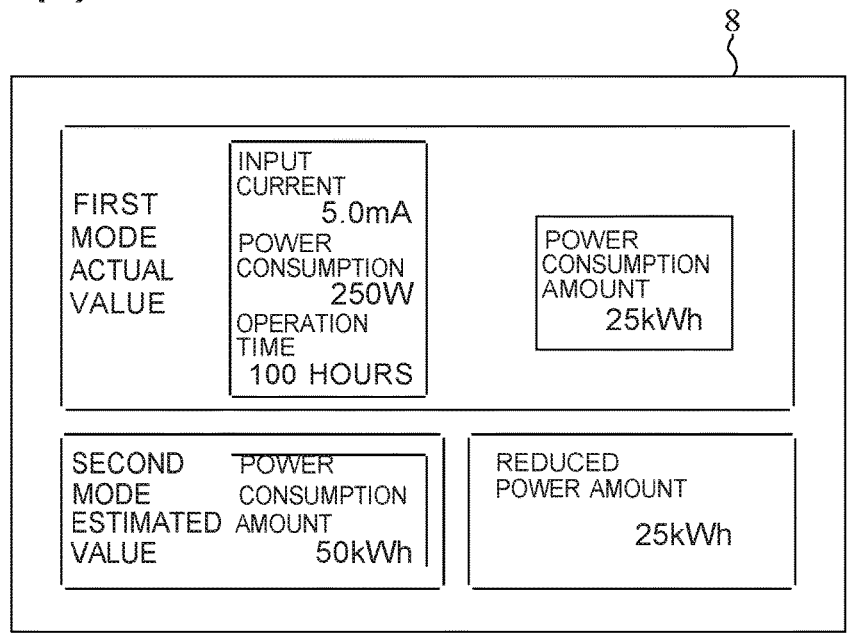
FIG. 3(a) is a table showing a setting example of an X-ray irradiation unit and an X-ray detection unit in the X-ray inspection apparatus of FIG. 1.
FIG. 3(b) is a schematic diagram showing a display unit of the X-ray inspection apparatus of FIG. 1.

As shown in FIG. 2 and FIG. 3(a), the control unit 10 sets the input current to the X-ray irradiation unit 6 to a test value (for example, 1.0 mA), in a state where the sensitivity of the X-ray detection unit 7 is set to a test value (for example, one time), and controls the X-ray irradiation unit 6 such that the irradiation output of the X-ray irradiation unit 6 becomes a test irradiation output (step S10). The control unit 10 acquires the test detection output of the X-ray detection unit 7 (step S11). Here, it is considered that there is acquired a relationship in which the test detection output of the X-ray detection unit 7 is 150 counts when the input current (test value) to the X-ray irradiation unit 6 is 1.0 mA.

Subsequently, as a second stage of the calibration processing, the control unit 10 sets the input current to the X-ray irradiation unit 6 and the sensitivity of the X-ray detection unit 7, by using the relationship acquired in the first stage, such that the detection range of the detection output of the X-ray detection unit 7 falls within the inspection range in either the first mode or the second mode.

The control unit 10 determines whether or not the first mode is selected in the X-ray inspection apparatus 1 (step S12). In step S12, in a case where the control unit 10 determines that the first mode is selected in the X-ray inspection apparatus 1, the control unit 10 sets the sensitivity of the X-ray detection unit 7 to the first sensitivity (step S13). Corresponding to the fact that the sensitivity of the X-ray detection unit 7 is set to the first sensitivity in step S13, the control unit 10 sets the input current to the X-ray irradiation unit 6 to the first input current, and controls the X-ray irradiation unit 6 such that the irradiation output of the X-ray irradiation unit 6 becomes the first irradiation output (step S14).

The first sensitivity is higher than the second sensitivity as described later. As an example, the first sensitivity is four times, in a case where the second sensitivity is set to be two times of when the input current to the X-ray irradiation unit 6 is the maximum value (10.0 mA) in the second mode. With this first sensitivity, in order for the detection range of the detection output of the X-ray detection unit 7 to fall within the inspection range, it is necessary to set the first input current to be five times (=20 times÷4 times) than the input current (test value) to the X-ray irradiation unit 6 in the first stage. Therefore, the first input current is set to 5.0 mA (=1.0 mA×5 times) in step S14.

Here, under the certain condition described above, even though the control unit 10 controls the X-ray irradiation unit 6 such that the irradiation output of the X-ray irradiation unit 6 becomes the first irradiation output, there is a case where the detection output of the X-ray detection unit 7 is decreased. In this case, there is a possibility that the deterioration in the X-ray irradiation unit 6 or the X-ray detection unit 7 is progressing. In the first mode in which the sensitivity of the X-ray detection unit 7 is fixed to the first sensitivity higher than the second sensitivity, since the input current to the X-ray irradiation unit 6 is set to the first input current smaller than the maximum value, there is room for increasing the input current to the X-ray irradiation unit 6. Therefore, the control unit 10 acquires the detection output of the X-ray detection unit 7 (step S15), and determines whether or not the detection output of the X-ray detection unit 7 is decreased (step S16).

In a case where the control unit 10 determines in step S16 that the detection output of the X-ray detection unit 7 is decreased, in order to compensate for the detection output of the X-ray detection unit 7 that has been decreased due to the progressed deterioration of the X-ray irradiation unit 6 or the X-ray detection unit 7, the control unit 10 executes the first control of controlling the X-ray irradiation unit 6 such that the irradiation output of the X-ray irradiation unit 6 is increased (step S17). That is, the control unit 10 increases the irradiation output of the X-ray irradiation unit 6 by increasing the input current to the X-ray irradiation unit 6, if the detection output of the X-ray detection unit 7 is decreased when the control unit 10 sets the sensitivity of the X-ray detection unit 7 to the first sensitivity higher than the second sensitivity and simultaneously controls the X-ray irradiation unit 6 such that the input current to the X-ray irradiation unit 6 becomes the first input current smaller than the maximum value. Therefore, the input current to the X-ray irradiation unit 6 becomes larger than the first input current (5.0 mA in the example) set in step S14, and the intensity of X-rays incident on the X-ray detection unit 7 increases. For this reason, the detection output of the X-ray detection unit 7 which has been decreased is increased. Therefore, it is possible to set the detection range of the detection output of the X-ray detection unit 7 to fall within the inspection range. After step S17, the processing proceeds to step S15, and the control unit 10 acquires the detection output of the X-ray detection unit 7 again, in a state where the irradiation output of the X-ray irradiation unit 6 is increased.

In step S16, in a case where the control unit 10 determines that the detection output of the X-ray detection unit 7 is not decreased, it is confirmed whether the inspection of the article G is possible or impossible with the set input current to the X-ray irradiation unit 6 and the set sensitivity of the X-ray detection unit 7. In the first mode, since the input current to the X-ray irradiation unit 6 is suppressed such that the sensitivity of the X-ray detection unit 7 is increased, there is a possibility that noises included in the X-ray transmission image generated by the control unit 10 increase. Therefore, the control unit 10 determines whether the inspection of the article G is possible or impossible, for example, based on whether or not the variation (an average, a deviation, and the like) of the detection output of the X-ray detection, unit 7 is within a predetermined range (step S18).

In a case where the control unit 10 determines in step S18 that the inspection of the article G is possible, the control unit 10 ends the calibration processing in the first mode. Thereafter, in the X-ray inspection apparatus 1, the inspection of the article G is performed with the set input current to the X-ray irradiation unit 6 and the set sensitivity of the X-ray detection unit 7.

In a case where the control unit 10 determines in step S18 that the inspection of the article G is impossible, the control unit 10 resets the input current to the X-ray irradiation unit 6 by increasing the input current to the X-ray irradiation unit 6 such that the variation (an average, a deviation, and the like) in the detection output of the X-ray detection unit 7 falls within a predetermined range (step S19). Therefore, it is possible to guarantee the performance of the inspection of the article G. Incidentally, in step S19, the control unit 10 may reset the input current to the X-ray irradiation unit 6 and the sensitivity of the X-ray detection unit 7 by increasing the sensitivity of the X-ray detection unit 7 together with the input current to the X-ray irradiation unit 6 such that the variation in the detection output of the X-ray detection unit 7 falls within a predetermined range. Thereafter, the control unit 10 ends the calibration processing in the first mode. In the X-ray inspection apparatus 1, the inspection of the article G is performed with the set input current to the X-ray irradiation unit 6 and the set sensitivity of the X-ray detection unit 7.

On the other hand, in a case where the control unit 10 determines in step S12 that the second mode is selected in the X-ray inspection apparatus 1, the control unit 10 sets the input current to the X-ray irradiation unit 6 to the maximum value (10.0 mA) and controls the X-ray irradiation unit 6 such that the irradiation output of the X-ray irradiation unit 6 becomes the second irradiation output (step S20). Corresponding to the fact that the input current to the X-ray irradiation unit 6 is set to the maximum value in step S20, the control unit 10 sets the sensitivity of the X-ray detection unit 7 to the second sensitivity (step S21).

As an example, the input current (maximum value: 10.0 mA) of the X-ray irradiation unit 6 set in step S20 is 10 times than a test value (1.0 mA) of the input current to the X-ray irradiation unit 6 in the first stage of the calibration processing. In this regard, in order for the detection range of the detection output of the X-ray detection unit 7 to hill within the inspection range, it is necessary to set the second sensitivity to be two times (=20 times÷10 times) than the test value (one time) of the sensitivity of the X-ray detection unit 7 in the first stage. Therefore, the second sensitivity is set to be two times in step S21.

Here, under the certain condition described above, even though the control unit 10 controls the X-ray irradiation unit 6 such that the irradiation output of the X-ray irradiation unit 6 becomes the second irradiation output, there is a case where the detection output of the X-ray detection unit 7 is decreased. In this case, there is a possibility that the deterioration in the X-ray irradiation unit 6 or the X-ray detection unit 7 is progressing. Therefore, the control unit 10 acquires the detection output of the X-ray detection unit 7 (step S22), and determines whether or not the detection output of the X-ray detection unit 7 is decreased (step S23).

In a case where the control unit 10 determines in step S23 that the detection output of the X-ray detection unit 7 is decreased, in order to compensate for the detection output of the X-ray detection unit 7 that has been decreased due to the progressed deterioration of the X-ray irradiation unit 6 or the X-ray detection unit 7, the control unit 10 executes the second control of controlling the X-ray detection unit 7 such that the detection output of the X-ray detection unit 7 is increased (step S24). That is, the control unit 10 increases the detection output of the X-ray detection unit 7 by increasing the sensitivity of the X-ray detection unit 7, if the detection output of the X-ray detection unit 7 is decreased when the control unit 10 controls the X-ray irradiation unit 6 such that the input current to the X-ray irradiation unit 6 becomes the maximum value. Therefore, the sensitivity of the X-ray detection unit 7 becomes higher than the second sensitivity (two times in the example) set in step S21, and the counted number of X-rays detected by the X-ray detection unit 7 increases. For this reason, the detection output of the X-ray detection unit 7 which has been decreased is increased. Therefore, it is possible to set the detection range of the detection output of the X-ray detection unit 7 to fall within the inspection range. After step S24, the processing proceeds to step S22, and the control unit 10 acquires the detection output of the X-ray detection unit 7 again in a state where the detection output of the X-ray detection unit 7 is increased.

In a case where the control unit 10 determines in step S23 that the detection output of the X-ray detection unit 7 is not decreased, the control unit 10 ends the calibration processing in the second mode. Thereafter, in the X-ray inspection apparatus 1, the inspection of the article G is performed with the set input current to the X-ray irradiation unit 6 and the set sensitivity of the X-ray detection unit 7.

Incidentally, in a case where the first mode is selected in the X-ray inspection apparatus 1, the control Unit 10 causes the display operation unit 8 to display a time during which the first control is being executed (hereinafter, also referred to as a first mode operation time) and information on the irradiation output of the X-ray irradiation unit 6 controlled by the first control. The "time during which the first control is being executed" displayed on the display operation unit 8 may include not only a time during which the processing of the first control (the processing of step S17 in FIG. 2) by increasing the input current to the X-ray irradiation unit 6 is executed, but also a time during which calibration processing (the processing of steps S10 to S19 in FIG. 2) is performed in a state where the first mode is selected and a time during which the inspection of the article G is performed with the input current of the X-ray irradiation unit 6 and the sensitivity of the X-ray detection unit 7 set by the calibration processing performed in the state where the first mode is selected.

For example, as shown in FIG. 3(b), in the first mode operation time, the control unit 10 displays an actual value of the input current (first input current) to the X-ray irradiation unit 6, an actual value of the power consumption (first irradiation output) in the X-ray irradiation unit 6, an actual value of the first mode operation time, and an actual value of the power consumption amount in the X-ray irradiation unit 6 on the display operation unit 8. Specifically, the actual value of the input current to the X-ray irradiation unit 6 is 5.0 mA, the actual value of the power consumption in the X-ray irradiation unit 6 is 250 W, the actual value of the first mode operation time (operation time) is 100 hours, and the actual value of the power consumption amount in the X-ray irradiation unit 6 is 25 kWh. In the example of FIG. 3(b), the input current and the sensitivity of the first mode shown in FIG. 3(a) are set as the input current and sensitivity the first mode.

The control unit 10 causes the display operation unit 8 to display an estimated value of the power consumption amount in the X-ray irradiation unit 6 in a case where it is assumed that the second mode is selected in the first mode operation time. Specifically, the estimated value of the power consumption amount in the X-ray irradiation unit 6 is 50 kWh. In the example of FIG. 3(b), the input current and the sensitivity of the second mode shows in FIG. 3(a) are set as the input current and sensitivity in the second mode.

The control unit 10 causes the display operation unit 8 to display a power amount of a difference between the estimated value of the power consumption amount in the second mode and the actual value of the power consumption amount in the first mode, as a reduced power amount, wherein the reduced power amount is a power amount which is estimated to have been reduced by operating the X-ray inspection apparatus 1 in the first mode. In the example shown in FIG. 3(b), the reduced power amount is 25 kWh.

As described above, in the X-ray inspection apparatus 1, there is a possibility that the deterioration of the X-ray irradiation unit 6 or the X-ray detection unit 7 is progressing, if the detection output of the X-ray detection unit 7 is decreased when the control unit 10 controls the X-ray irradiation unit 6 such that the irradiation output of the X-ray irradiation unit 6 becomes the first irradiation output. At this time, the deterioration of the X-ray irradiation unit 6 and the X-ray detection unit 7 is suppressed, as compared with a case where the irradiation output of the X-ray irradiation unit 6 is the maximum value, if the sensitivity of the X-ray detection unit 7 is previously set to a relatively high first sensitivity and the first irradiation output of the X-ray irradiation unit 6 is set to be smaller than the maximum value. Also, the control unit 10 executes the first control to secure room for increasing the irradiation output of the X-ray irradiation unit 6 so that it is possible to prevent the inspection performance of the article G from being reduced. Therefore, it is possible to suppress the deterioration of the X-ray irradiation unit 6 and the X-ray detection unit 7 while securing the inspection performance of the article G. Also, as a result, it is possible to delay the lifetime (prolong the lifetime) of the X-ray irradiation unit 6 and the X-ray detection unit 7.

In the X-ray inspection apparatus 1, the control unit executes the first control in a state where the article G is not irradiated with the X-rays emitted by the X-ray irradiation unit 6 and the X-ray detection unit 7 is detecting the X-rays with which the article G is not irradiated. Under this condition, it is highly likely that the detection output of the X-ray detection unit 7 is decreased due to the deterioration of the X-ray irradiation unit 6 or the X-ray detection unit 7, as compared with a state where the X-ray detection unit 7 detects X-rays transmitted through the article G. Therefore, the control unit 10 can appropriately execute the first control.

In the X-ray inspection apparatus 1, the control unit 10 executes the second control of controlling the X-ray detection unit 7 such that the detection output of the X-ray detection unit 7 is increased, if the detection output of the X-ray detection unit 7 is decreased when the control unit 10 controls the X-ray irradiation unit 6 such that the irradiation output of the X-ray irradiation unit 6 becomes the second irradiation output larger than the first irradiation output. The first control (first mode) and the second control (second mode) are switchable. Therefore, the operator of the X-ray inspection apparatus 1 can select either the first control in which the irradiation output of the X-ray irradiation unit 6 is suppressed or the second control in which the irradiation output of the X-ray irradiation unit 6 is enhanced.

In the X-ray inspection apparatus 1, in the second control, the control unit 10 increases the detection output of the X-ray detection unit 7 by increasing the sensitivity of the X-ray detection unit 7, if the detection output of the X-ray detection unit 7 is decreased when the control unit 10 sets the sensitivity of the X-ray detection unit 7 to the second sensitivity and simultaneously controls the X-ray irradiation unit 6 such that the input current to the X-ray irradiation unit 6 becomes the maximum value. In the first control, the control unit 10 increases the irradiation output of the X-ray irradiation unit 6 by increasing the input current to the X-ray irradiation unit 6, if the detection output of the X-ray detection unit 7 is decreased when the control unit 10 sets the sensitivity of the X-ray detection unit 7 to the first sensitivity higher than the second sensitivity and simulta-neously controls the X-ray irradiation unit 6 such that the input current to the X-ray irradiation unit 6 becomes the first input current smaller than the maximum value. Therefore, since the control unit 10 executes the first control of controlling the X-ray irradiation unit 6 with the input current having the input current to the X-ray irradiation unit 6 smaller than the maximum value, it is possible to reduce the power consumption of the X-ray irradiation unit 6.

The X-ray inspection apparatus 1 includes the display operation unit 8 for displaying a time during which the first control is being executed by the control unit 10 and information (the input current to the X-ray irradiation unit 6, the power consumption amount of the X-ray irradiation unit 6, and the reduced power amount by the first control) on the irradiation output of the X-ray irradiation unit 6 controlled by the first control. With the display operation unit 8, the operator of the X-ray inspection apparatus 1 can confirm that the deterioration of the X-ray irradiation unit 6 and the X-ray detection unit 7 is suppressed.

The present disclosure is not limited to the embodiments described above.

In the embodiments, the control unit 10 has executed the first control or the second control, in a case where the detection output of the X-ray detection unit 7 is decreased under the certain condition that factors causing the irradiation output of the X-ray irradiation unit 6 and the detection output of the X-ray detection unit 7 to fluctuate are reduced, because it is assumed that the deterioration in the X-ray irradiation unit 6 or the X-ray detection unit 7 is progressing. However, the control unit 10 may execute the first control and the second control under such a condition that, for example, even if the irradiation output of the X-ray irradiation unit 6 is substantially constant, there is provided a factor causing the detection output of the X-ray detection unit 7 to fluctuate with a constant fluctuation pattern. Under the condition, for example, the control unit 10 may store a reference fluctuation pattern of the detection output of the X-ray detection unit 7, extract a decrease in the detection output of the X-ray detection unit 7 by canceling the fluctuation of the detection output caused by the factor, determine that the deterioration of the irradiation output of the X-ray irradiation unit 6 or the detection output of the X-ray detection unit 7 has progressed, and execute the first control and the second control.

In the embodiments, the control unit 10 controls the X-ray irradiation unit 6 such that the input current to the X-ray irradiation unit 6 in the second control becomes the maximum value, but the input current to the X-ray irradiation unit 6 in the second control may not be the maximum value as long as it is larger than the input current to the X-ray irradiation unit 6 in the first control.

In the embodiments, as an example, the control unit 10 executes the calibration processing after starting up the X-ray inspection apparatus 1 and before starting the inspection of the article G by the X-ray inspection apparatus 1. However, for example, the calibration processing may be executed between inspections of the article G or the like.

In the embodiments, there is shown an example in which the control unit 10 functions as an inspection unit, and the control unit 10 and the inspection unit are configured to be physically integrated. However, the control unit 10 and the inspection unit may be physically configured as a separate body.

In the embodiments, the display operation unit 8 of the X-ray inspection apparatus 1 functions as a display unit. However, a display or the like provided separately from the X-ray inspection apparatus 1 may function as a display unit.

The present disclosure is applicable to an optical inspection apparatus other than an X-ray inspection apparatus that generates a light transmission image by detecting light (near infrared rays or other electromagnetic waves) transmitted through an article and performs the inspection of the article based on the light transmission image. However, in the case of using X-rays as light, even though the article G is packaged, it is possible to inspect chipping of the article G without affecting a packaging material or a printing applied to the packaging material.

The invention claimed is:

1. An X-ray inspection apparatus comprising:
   an X-ray irradiation unit that irradiates an article with X-rays;
   an X-ray detection unit that detects the X-rays transmitted through the article;
   an inspection unit that generates an X-ray transmission image of the article based on a signal output from the X-ray detection unit and performs inspection of the article based on the X-ray transmission image; and
   a control unit that controls the X-ray irradiation unit and the X-ray detection unit,
   wherein, the control unit executes a first control of controlling the X-ray irradiation unit such that an irradiation output is increased if a detection output of the X-ray detection unit is decreased when the control unit controls the X-ray irradiation unit such that the irradiation output of the X-ray irradiation unit becomes a first irradiation output, and
   the control unit executes the first control in a state where the article is not irradiated with the X-rays emitted by the X-ray irradiation unit and the X-ray detection unit is detecting the X-rays with which the article is not irradiated.

2. The X-ray inspection apparatus according to claim 1, wherein, the control unit executes a second control of controlling the X-ray detection unit such that the detection output is increased, if the detection output is decreased when the control unit controls the X-ray irradiation unit such that the irradiation output becomes a second n output larger than the first irradiation output, and
   the first control and the second control are switchable.

3. The X-ray inspection apparatus according to claim 2, wherein in the second control, the control unit increases the detection output by increasing a sensitivity, if the detection output is decreased when the control unit sets the sensitivity of the X-ray detection unit to a second sensitivity and simultaneously controls the X-ray irradiation unit such that an input current to the X-ray irradiation unit becomes a maximum value, and
   in the first control, the control unit increases the irradiation output by increasing the input current, if the detection output is decreased when the control unit sets the sensitivity to a first sensitivity higher than the second sensitivity and simultaneously controls the X-ray irradiation unit such that the input current becomes a first input current smaller than the maximum value.

4. The X-ray inspection apparatus according to claim 2, further comprising:
   a display unit that displays a time during which the control unit is executing the first control and information on the irradiation output of the X-ray irradiation unit controlled by the first control.

5. The X-ray inspection apparatus according to claim 3, further comprising:
   a display unit that displays a time during which the control unit is executing the first control and information on the irradiation output of the X-ray irradiation unit controlled by the first control.

* * * * *